(12) United States Patent
Elokdah et al.

(10) Patent No.: US 7,056,943 B2
(45) Date of Patent: Jun. 6, 2006

(54) SUBSTITUTED INDOLE OXO-ACETYL AMINO ACETIC ACID DERIVATIVES AS INHIBITORS OF PLASMINOGEN ACTIVATOR INHIBITOR-1 (PAI-1)

(75) Inventors: Hassan Mahmoud Elokdah, Yardley, PA (US); Geraldine Ruth McFarlane, Monmouth Junction, NJ (US); David Zenan Li, Princeton, NJ (US)

(73) Assignee: Wyeth, Madison, NJ (US)

( * ) Notice: Subject to any disclaimer, the term of this patent is extended or adjusted under 35 U.S.C. 154(b) by 120 days.

(21) Appl. No.: 10/731,074

(22) Filed: Dec. 9, 2003

(65) Prior Publication Data

US 2004/0116504 A1 Jun. 17, 2004

Related U.S. Application Data

(60) Provisional application No. 60/432,331, filed on Dec. 10, 2002.

(51) Int. Cl.
*A61K 43/38* (2006.01)
*C07D 209/90* (2006.01)

(52) U.S. Cl. ............... 514/419; 548/492; 548/490
(58) Field of Classification Search ............ 548/490, 548/492; 514/419
See application file for complete search history.

(56) References Cited

U.S. PATENT DOCUMENTS

| | | | |
|---|---|---|---|
| 3,843,683 A | 10/1974 | Bell ........................... | 548/493 |
| 4,736,043 A | 4/1988 | Michel et al. .............. | 548/492 |
| 4,851,406 A * | 7/1989 | Mertens et al. ........ | 514/217.04 |
| 5,612,360 A | 3/1997 | Boyd et al. ................. | 514/381 |
| 6,048,875 A | 4/2000 | De Nanteuil et al. ....... | 514/314 |
| 6,110,963 A | 8/2000 | Malamas .................... | 514/443 |
| 6,232,327 B1 * | 5/2001 | Nickel et al. ............... | 514/337 |
| 6,251,936 B1 | 6/2001 | Wrobel et al. ............. | 514/443 |
| 6,302,837 B1 | 10/2001 | De Nanteuil et al. ....... | 514/337 |
| 6,787,556 B1 | 9/2004 | Hargreaves et al. ........ | 514/311 |
| 6,800,645 B1 | 10/2004 | Cox et al. ................... | 514/314 |
| 6,800,654 B1 | 10/2004 | Mayer et al. ............... | 514/381 |
| 6,844,358 B1 | 1/2005 | Malamas et al. ........... | 514/336 |
| 2003/0060497 A1 | 3/2003 | Gerlach ...................... | 514/414 |
| 2004/0204417 A1 | 10/2004 | Perez et al. ................. | 514/249 |

FOREIGN PATENT DOCUMENTS

| | | |
|---|---|---|
| DE | 43 38 770 A1 | 5/1995 |
| DE | 19543639 A1 | 5/1997 |
| DE | 19753522 | 6/1999 |
| EP | 0 416 609 A2 | 3/1991 |
| EP | 0 508 723 A1 | 10/1992 |
| EP | 0 512 570 A1 | 11/1992 |
| EP | 0 540 956 A1 | 5/1993 |
| EP | 0 655 439 A2 | 5/1995 |
| EP | 0 819 686 A1 | 1/1998 |
| EP | 0 955 299 A1 | 11/1999 |
| EP | 1 092 716 A2 | 4/2001 |
| EP | 1 156 045 A1 | 11/2001 |
| GB | 1 321 433 | 6/1973 |
| WO | 94/14434 A1 | 7/1994 |
| WO | 94/26738 A1 | 11/1994 |
| WO | 95/10513 A1 | 4/1995 |
| WO | 96/06840 A1 | 3/1996 |
| WO | 96/21656 A1 | 7/1996 |
| WO | WO 9626207 A1 * | 8/1996 |
| WO | WO 96/32379 | 10/1996 |
| WO | 97/09308 A1 | 3/1997 |

(Continued)

OTHER PUBLICATIONS

Ashitani J. Mukae H. Arimura Y. Matsukura S. Elevated plasma procoagulant and fibrinolytic markers in patients with chronic obstructive pulmonary disease. [Journal Article] Internal Medicine. 41(3):181-5, Mar. 2002.*

(Continued)

*Primary Examiner*—Kamal A. Saeed
*Assistant Examiner*—Michael Barker
(74) *Attorney, Agent, or Firm*—Woodcock Washburn LLP

(57) ABSTRACT

This invention provides indole oxo-acetyl amino acetic acid derivatives which are useful as inhibitors of plasminogen activator inhibitor-1 (PAI-1) useful for treating fibrinolytic disorders, the compounds having the structure:

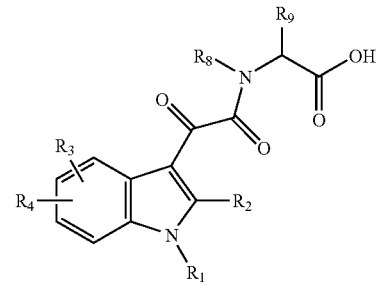

wherein: $R_1$ is alkyl or optionally substituted cycloalkyl, —$CH_2$-cycloalkyl, pyridinyl, —$CH_2$-pyridinyl, phenyl or benzyl; $R_2$ is hydrogen, alkyl, cycloalkyl, —$CH_2$-cycloalkyl, or perfluoroalkyl; $R_3$ is hydrogen, halo, alkyl, perfluoroalkyl, alkoxy, cycloalkyl, —$CH_2$-cycloalkyl, —$NH_2$, or —$NO_2$; $R_4$ is optionally substituted phenyl, benzyl, benzyloxy, pyridinyl, or —$CH_2$-pyridinyl; $R_8$ is hydrogen, alkyl, cycloalkyl, —$CH_2$-cycloalkyl, perfluoroalkyl, aryl, substituted aryl, alkyl-aryl, or substituted alkyl-aryl; $R_9$ is hydrogen, alkyl, hydroxyalkyl, 4-hydroxybenzyl, 3-indolylmethylene, 4-imidazolylmethylene, $HSCH_2$—, $CH_3SCH_2CH_2$—, $H_2NC(\!=\!O)CH_2$—, $H_2NC(\!=\!O)CH_2CH_2$—, $HO_2CCH_2$—, $HO_2CCH_2CH_2$—, $H_2NCH_2CH_2CH_2CH_2$—, $H_2NC(\!=\!NH)NHCH_2CH_2CH_2$—, or taken together with $R_8$ as —$CH_2CH_2CH_2$—; or a pharmaceutically acceptable salt or ester form thereof.

9 Claims, No Drawings

FOREIGN PATENT DOCUMENTS

| WO | 97/43260 A1 | 11/1997 |
|---|---|---|
| WO | 97/48697 A1 | 12/1997 |
| WO | 98/08818 A1 | 3/1998 |
| WO | WO 99/28297 | 6/1999 |
| WO | 99/43672 A1 | 9/1999 |
| WO | 99/46260 A1 | 9/1999 |
| WO | WO 99/43651 | 9/1999 |
| WO | WO 99/43654 | 9/1999 |
| WO | 99/50268 A1 | 10/1999 |
| WO | 99/58519 A1 | 11/1999 |
| WO | 99/61435 A1 | 12/1999 |
| WO | 00/32180 A2 | 6/2000 |
| WO | 00/35919 A1 | 6/2000 |
| WO | 00/46195 A1 | 8/2000 |
| WO | 00/046197 A1 | 8/2000 |
| WO | 01/12187 A2 | 2/2001 |
| WO | 02/030895 A1 | 4/2002 |
| WO | 02/072549 A1 | 9/2002 |
| WO | 03/000253 A1 | 1/2003 |
| WO | 03/031409 A1 | 4/2003 |
| WO | WO 3068742 A1 * | 8/2003 |
| WO | 03/087087 A2 | 10/2003 |
| WO | 2004/052854 A2 | 6/2004 |

OTHER PUBLICATIONS

Razavi MK. Wong H. Kee ST. Sze DY. Semba CP. Dake MD. Initial clinicalresults of tenecteplase (TNK) in catheter-directed thrombolytic therapy.[Clinical Trial. Journal Article] J. of Endovascular Therapy: Official Journal of the International Society of Endovascular Therapy: Official Journal of the International Society of Endovascular Specialists. 9(5) : 593-8. Oct. 2002.*

Rocha-Singh KJ. Trokey J. Combined glycoprotein IIb/IIIA receptor inhibition and low-dose fibrinolysis for peripheral arterial thrombosis.[Clinical Trial. Journal Article] Catheterization & Cardiovascular Interventions. 55(4):457-60, Apr. 2002.*

Albers GW. Advances in intravenous thrombolytic therapy for treatment of acute stroke. [Review] [37 refs] [Journal Article. Review] Neurology. 57(5 Suppl 2):S77-81, 2001.*

Hamano K. Iwano M. Akai Y. Sato H. Kubo A. Nishtani Y. Uyama H. Yoshida Y. Miyazaki M. Shiiki H. Kohno S. Dohi K. expression of glomerular plasminogen activator inhibitor type 1 in glomerulonephritis. [Journal Article] American Journal of Kidney Diseases. 39(4) : 695-705, Apr. 2002.*

Thogersen AM. Jansson JH. Boman K. Nilsson TK. Weinehall L. Huhtasaari F. Hallmans G. High plasminogen activator inhibitor and tissue plasminogen activator levels in plasma precede a first acute myocardial infarction in both men and women: evidence for the fibrinolytic system as an independent primary risk factor. [Journal Article] Circulation. 98(21) : 2241-7, Nov. 24, 1998.*

Takanashi K. Inukai T. Insulin resistance and changes in the blood coagulation-fibrinolysis system after a glucose clamp technique in patients with type 2 diabetes mellitus. [Journal Article] Journal of Medicine.31(1-2):45-62, 2000.*

Takazoe K. Ogawa H. Yasue H. Sakamoto T. Soejima H. Miyao Y. Kawano H. Moriyama Y. Misumi K. Suefuji H. Kugiyama K. Yoshimura M. Increased plasminogen activator inhibitor activity and diabetes predict subsequent coronary events in patients with angina pectoris. [Journal Article] Annals. of Medicine. 33(3) : 206-12, Apr. 2001.*

Mari D. Parnetti L. Coppola R. Bottasso B. Reboldi GP. Senin U. Mannucci PM. Hemostasis abnormalities in patients with vascular dementia and Alzheimer's disease. [Journal Article] Thrombosis & Haemostasis. 75(2):216-8, Feb. 1996.*

Hino H. Akiyama H. Iseki E. Kato M. Kondo H. Ikeda K. Kosaka K. Immunohistochemical localization of plasminogen activator inhibitor-1 in rat and human brain tissues. [Journal Article] Neuroscience Letters. 297(2):105-8, Jan. 12, 2001.*

Atiomo WU. Hilton D. Fox R. Lee D. Shaw S. Friend J. Wilkin TJ. Prentice AG. Immunohistochemical detection of plasminogen activator inhibitor-1 in polycystic ovaries. [Journal Article] Gynecological Endocrinology. 14(3): 162-8, Jun. 2000.*

Glueck CJ. Phillips H. Cameron D. Sieve-Smith L. Wang P. Continuing metformin throughout pregnancy in women with polycystic ovary syndrome appears to safely reduce first-trimester spontaneous abortion: a pilot study. [Clinical Trial. Journal Article] Fertility & Sterility. 75(1): 46-52, Jan. 2001.*

Billgren AM. Rutqvist LE. Johansson H. Hagerstrom T. Skoog L. The role of cathepsin D and PAI-1 in primary invasive breast cancer as prognosticators and predictors of treatment benefit with adjuvant tamoxifen. [Journal Article] European Journal of Cancer. 36(11): 1374-80, Jul. 2000.*

Wind T. Jensen MA. Andreasen PA. Epitope mapping for four monoclonal antibodies against human plasminogen activator inhibitor type-1: implications for antibody-mediated PAI-1-neutralization and vitronectin-binding. [Journal Article] European Journal of Biochemistry. 268(4): 1095-106, Feb. 2001.*

Berry CN. Lunven C. Lechaire I. Girardot C. O'Connor SE. Antithrombotic activity of a monoclonal antibody inducing the substrate form of plasminogen activator inhibitor type 1 in rat models of venous and arterial thrombosis. [Journal Article] British Journal of Pharmacology. 125(1) : 29-34, Sep. 1998.*

Lahlou A. Peraldi MN. Thervet E. Flahault A. Delarue F. Soubrier F. Rossert J. Hertig A. Rondeau E. Chronic graft dysfunction in renal transplant patients: potential role of plasminogen activator inhibitor type 1. [Journal Article] Transplantation. 73(8)1290-5, Apr. 27, 2002.*

Sobel BE. The potential influence of insulin and plasminogen activator inhibitor type 1 on the formation of vulnerable atherosclerotic plaques associated with type 2 diabetes. [Editorial] Proceedings of the Association of American Physicians. 111(4):313-8, Jul.-Aug. 1999.*

Roldan V. Marin F. Marco P. Martinez JG. Calatayud R. Sogorb F. Hypofibrinolysis in atrial fibrillation. [Journal Article] American Heart Journal. 136(6):956-60, Dec. 1998.*

Chitra Krishnamurti et al., Blood, Mar. 1987, 798-803, 69(3).

Christopher F. Reilly et al., Arteriosclerosis and Thrombosis, Sep./Oct. 1991, 1276-1286, 11(5).

Peter Carmeliet et al., J. Clin. Investigations, 1993, 2756-2760, 92.

E. Rocha et al., Fibrinolysis, 1994, 294-303, 8.

Justo Aznar et al., Haemostasis, 1994, 243-251, 24.

B.J. Biemond et al., Circulation, 1995, 1175-1181, 91(4).

Marcel Levi et al., Circulation, Jan. 1992, 305-312, 85(1).

Thomas K. Nordt et al., J. Clin. Endocrinology and Metabolism, 2000, 1563-1568, 85(4).

E. Daci et al., J. Bone and Mineral Research, 2000, 1510-1516, 15(8).

Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 2: 1422-1428.

Guzzo, P.R. et al., "Synthesis of a conformationally constrained threonin-valine dipeptide mimetic: design of a potential inhibitor of plasminogen activator inhibitor-1," *Tetrahedron Letters*, 43(1), 41-43 (2002).

Charlton, Peter, "The status of plasminogen activator inhibitor-1 as a therapeutic target," Expert *Opinion On Investigational Drugs*, (May 1997), vol. 6, No. 5, pp. 539-554.

Malamas, M.S. et al., "Characterization and comparative evaluation of a structurally unique PAI-1 inhibitor exhibiting oral in-vivo efficacy," *Journal of Medicinal Chemistry*, 43(7):1293-1310.

Da Settimo, A. et al., "Reaction of indole derivatives with bromine, substitution, oxidation,and dimerization," *J Org Chem*, 1970, 35(8):2546-2551.

* cited by examiner

SUBSTITUTED INDOLE OXO-ACETYL AMINO ACETIC ACID DERIVATIVES AS INHIBITORS OF PLASMINOGEN ACTIVATOR INHIBITOR-1 (PAI-1)

This application claims priority from co-pending provisional application Ser. No. 60/432,331 filed on Dec. 10, 2002, the entire disclosure of which is hereby incorporated by reference.

This invention relates to the composition and the utility of indole oxo-acetyl amino acetic acid derivatives which are useful as inhibitors of plasminogen activator inhibitor-1 (PAI-1) and therapeutic compositions for treating conditions resulting from fibrinolytic disorders such as deep vein thrombosis and coronary heart disease, and pulmonary fibrosis.

BACKGROUND OF INVENTION

Plasminogen activator inhibitor-1 (PAI-1) is a major regulatory component of the plasminogen-plasmin system. PAI-1 is the principal physiologic inhibitor of both tissue type plasminogen activator (t-PA) and urokinase type plasminogen activator (u-PA). Elevated plasma levels of PAI-1 have been associated with thrombotic events as indicated by animal experiments (Krishnamurti, *Blood*, 69, 798 (1987); Reilly, *Arteriosclerosis and Thrombosis*, 11, 1276 (1991); Carmeliet, *Journal of Clinical Investigations*, 92, 2756 (1993)) and clinical studies (Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases of women such as polycystic ovary syndrome (Nordt, *Journal of clinical Endocrinology and Metabolism*, 85, 4, 1563 (2000)) and bone loss induced by estrogen deficiency (Daci, *Journal of Bone and Mineral Research*, 15, 8, 1510 (2000)). Accordingly, agents that inhibit PAI-1 would be of utility in treating conditions originating from fibrinolytic disorder such as deep vein thrombosis, coronary heart disease, pulmonary fibrosis, polycystic ovary syndrome, etc.

WO 99/43654 and WO 99/43651 disclose indole derivatives of formula I as inhibitors phospholipase enzymes useful in preventing inflammatory conditions.

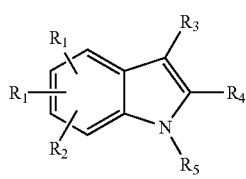

(I)

U.S. Pat. No. 4,851,406 discloses cardiotonic compounds of formula:

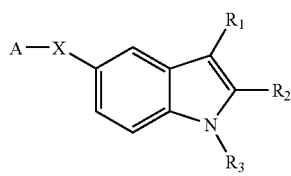

(I)

wherein A is a five-membered, or six-membered ring heterocycle; X is a bond, an alkylene, or a vinylene radical; $R_1$ is H, alkyl, alkenyl, cycloalkyl, cycloalkenyl, carboxyl, cyano, alkylcarbonyl, alkoxycarbonyl, aminocarbonyl, alkylaminocarbonyl, dialkylaminocarbonyl or aryl radical; $R_2$ is H, alkyl, trihalogenomethyl, hydroxyl, cycloalkyl, cyano, carboxyyl, etc. cloalkenyl, carboxyl, cyano, alkylcarbonyl, alkoxycarbonyl, aminocarbonyl, alkylaminocarbonyl, dialkylaminocarbonyl or aryl radical; and $R_3$ is a hydrogen atom.

WO 96/32379 discloses PDE-inhibitor compounds of formula I where:

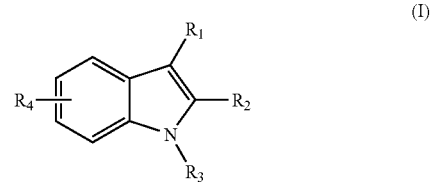

(I)

wherein $R_1$ is hydrogen, halogen, nitrogen, carboxy, protected carboxy, lower alkenyl, or acyl; $R_2$ is hydrogen, halogen, carboxy, lower alkenyl, or acyl; $R_3$ is lower alkenyl, or lower alkenyl, both optionally substituted; and $R_4$ is carboxy, protected carboxy, or acyl WO 9928297 discloses substituted indoles of formula I which have thrombin inhibiting effect and fibrinogen receptor antagonist effect:

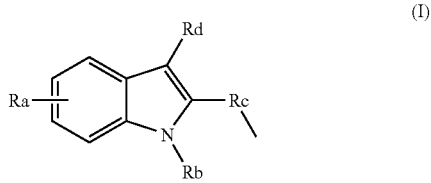

(I)

wherein: Ra is halogen, carboxy, $R_3R_4N$—CO—, $R_3R_4SO_2$—, or $R_4R5N$—; Rb and Rd are either alkyl or $R_2$—A where $R_2$ is a phenyl optionally substituted and A is an alkylene or a substituted alkylene; and Rc is a hydrogen, or alkyl.

EP 0 655 439 discloses 5,6 fused ring bicyclic compounds of the general formula I which are useful as platelet aggregation inhibitors.

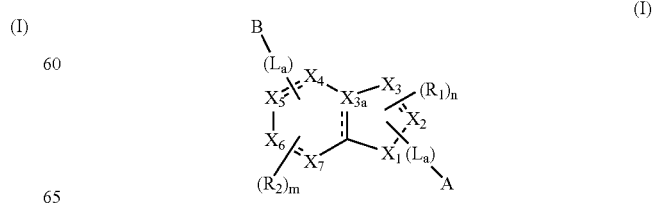

(I)

SUMMARY OF THE INVENTION

The present invention relates to compounds of formula I:

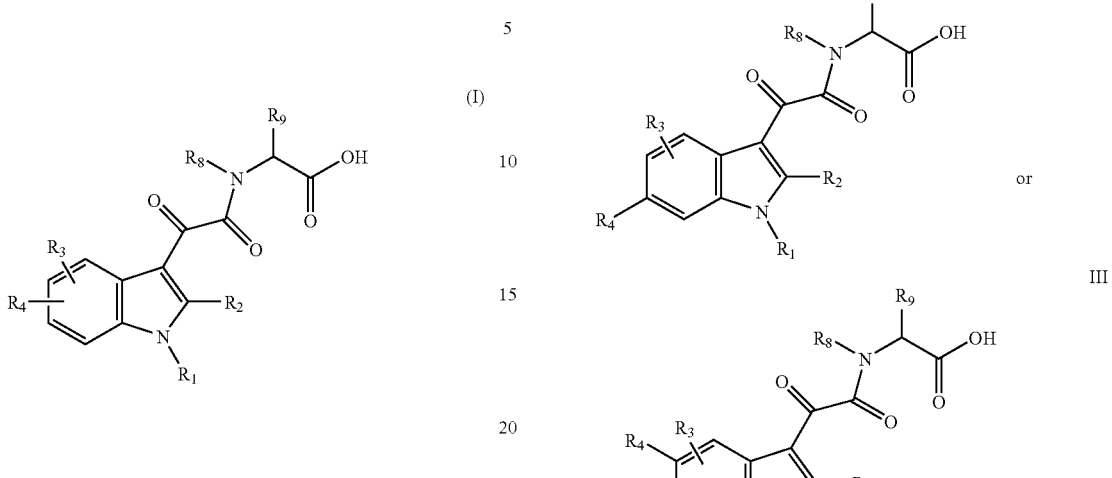

wherein:

R$_1$ is C$_1$–C$_8$ alkyl, preferably C$_1$–C$_6$ alkyl, C$_3$–C$_6$ cycloalkyl, —CH$_2$—C$_3$–C$_6$ cycloalkyl, pyridinyl, —CH$_2$-pyridinyl, phenyl or benzyl, wherein the rings of the cycloalkyl, pyridinyl, phenyl and benzyl groups may be optionally substituted by 1 to 3 groups selected from the group consisting of halogen, C$_1$–C$_6$ alkyl, C$_1$–C$_3$ perfluoroalkyl, —O—C$_1$–C$_3$ perfluoroalkyl, C$_1$–C$_3$ alkoxy, —OH, —NH$_2$, and —NO$_2$;

R$_2$ is hydrogen, C$_1$–C$_6$ alkyl, C$_3$–C$_6$ cycloalkyl, —CH$_2$—C$_3$–C$_6$ cycloalkyl, or C$_1$–C$_3$ perfluoroalkyl;

R$_3$ is hydrogen, halogen, C$_1$–C$_6$ alkyl, C$_1$–C$_3$ perfluoroalkyl, C$_1$–C$_6$ alkoxy, C$_3$–C$_6$ cycloalkyl, —CH$_2$—C$_3$–C$_6$ cycloalkyl, —NH$_2$, or —NO$_2$;

R$_4$ is phenyl, benzyl, benzyloxy, pyridinyl, or —CH$_2$-pyridinyl, wherein the rings of these groups may be optionally substituted by 1 to 3 groups selected from the group consisting of halogen, C$_1$–C$_3$ alkyl, C$_1$–C$_3$ perfluoroalkyl, —O—C$_1$–C$_3$ perfluoroalkyl, —C$_1$–C$_3$ alkoxy, —OH, —NH$_2$, and —NO$_2$;

R$_8$ is hydrogen, C$_1$–C$_6$ alkyl, C$_3$–C$_6$ cycloalkyl, —CH$_2$—C$_3$–C$_6$ cycloalkyl, or C$_1$–C$_3$ perfluoroalkyl, aryl, substituted aryl, alkyl-aryl, or substituted alkyl-aryl; and R$_9$ is hydrogen, C$_1$–C$_6$ alkyl, C$_3$–C$_6$ branched alkyl, C$_1$–C$_6$ hydroxyalkyl, 4-hydroxybenzyl, 3-indolylmethylene, 4-imidazolylmethylene, HSCH$_2$—, CH$_3$SCH$_2$CH$_2$—, H$_2$NC(=O)CH$_2$—, H$_2$NC(=O)CH$_2$CH$_2$—, HO$_2$CCH$_2$—, HO$_2$CCH$_2$CH$_2$—, H$_2$NCH$_2$CH$_2$CH$_2$CH$_2$—, H$_2$NC(=NH)NHCH$_2$CH$_2$CH$_2$—, or taken together with R$_8$, —CH$_2$CH$_2$CH$_2$—;

or a pharmaceutically acceptable salt or ester form thereof.

DETAILED DESCRIPTION OF THE INVENTION

Preferred compounds of this invention are those of formulas II and III:

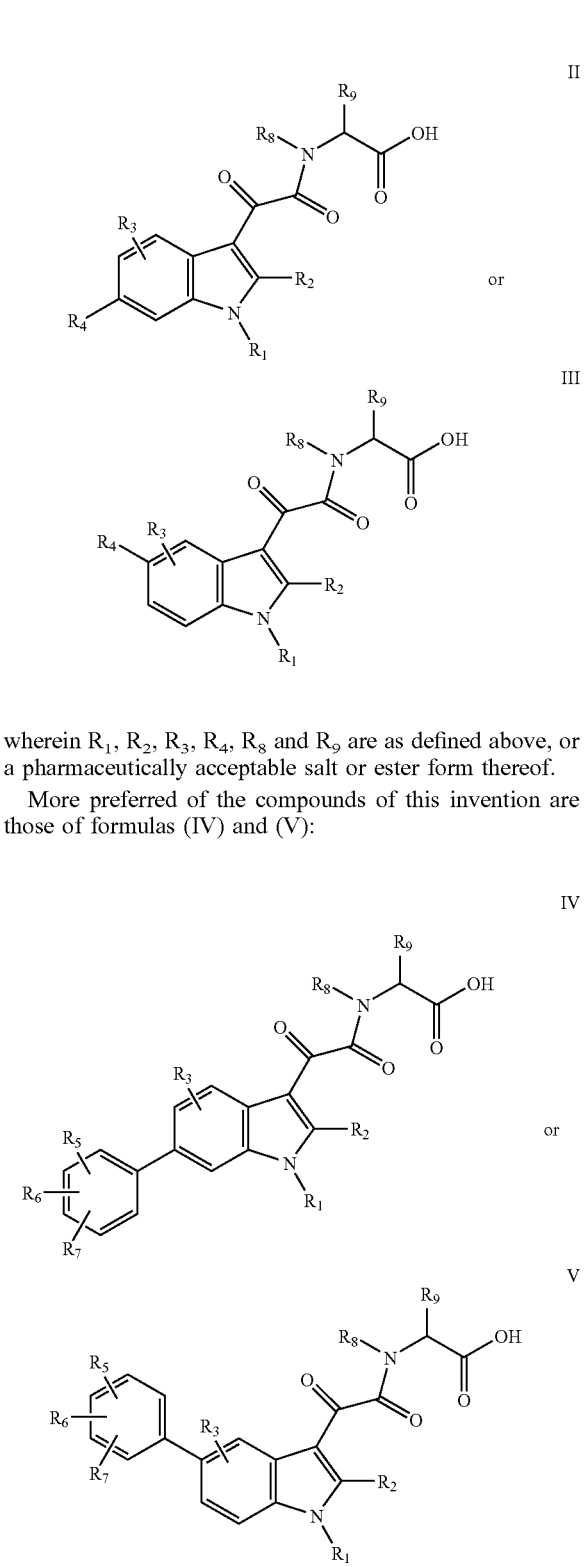

wherein R$_1$, R$_2$, R$_3$, R$_4$, R$_8$ and R$_9$ are as defined above, or a pharmaceutically acceptable salt or ester form thereof.

More preferred of the compounds of this invention are those of formulas (IV) and (V):

wherein:

R$_1$ is C$_1$–C$_8$ alkyl, preferably C$_1$–C$_6$ alkyl, C$_3$–C$_6$ cycloalkyl, —CH$_2$—C$_3$–C$_6$ cycloalkyl, or benzyl, wherein the rings of the cycloalkyl and benzyl groups may be optionally substituted by from 1 to 3 groups selected from halogen, C$_1$–C$_6$ alkyl, C$_1$–C$_3$ perfluoroalkyl, preferably —$CF_3$, —O—$C_1$—$C_3$ perfluoroalkyl, preferably —O—$CF_3$, $C_1$–$C_3$ alkoxy, —OH, —$NH_2$, or —$NO_2$;

$R_2$ is hydrogen, $C_1$–$C_6$ alkyl, $C_3$–$C_6$ cycloalkyl, —$CH_2$— $C_3$—$C_6$ cycloalkyl, or $C_1$–$C_3$ perfluoroalkyl;

$R_3$ is hydrogen, halogen, $C_1$–$C_6$ alkyl, $C_1$–$C_3$ perfluoroalkyl, $C_1$–$C_6$ alkoxy, $C_3$–$C_6$ cycloalkyl, —$CH_2$—$C_3$—$C_6$ cycloalkyl, —$NH_2$, or —$NO_2$;

$R_5$, $R_6$ and $R_7$ are each independently hydrogen, halogen, $C_1$–$C_3$ alkyl, $C_1$–$C_3$ perfluoroalkyl, —O—$C_1$—$C_3$ perfluoroalkyl, $C_1$–$C_3$ alkoxy, —OH, —$NH_2$, or —$NO_2$;

$R_8$ is hydrogen, $C_1$–$C_6$ alkyl, $C_3$–$C_6$ cycloalkyl, —$CH_2$— $C_3$—$C_6$ cycloalkyl, or $C_1$–$C_3$ perfluoroalkyl, aryl, substituted aryl, alkyl-aryl, or substituted alkyl-aryl;

$R_9$ is hydrogen, $C_1$–$C_6$ alkyl, $C_3$–$C_6$ branched alkyl, $C_1$–$C_6$ hydroxyalkyl, 4-hydroxybenzyl, 3-indolylmethylene, 4-imidazolylmethylene, $HSCH_2$—, $CH_3SCH_2CH_2$—, $H_2NC(=O)CH_2$—, $H_2NC(=O)CH_2CH_2$—, $HO_2CCH_2$—, $HO_2CCH_2CH_2$—, $H_2NCH_2CH_2CH_2CH_2$—, $H_2NC(=NH)NHCH_2CH_2CH_2$—, or taken together with $R_8$,—$CH_2CH_2CH_2$—;

or a pharmaceutically acceptable salt or ester form thereof.

Specific compounds according to the present invention are:

{[[1-(4-tert butylbenzyl)-5-(3-methylphenyl)-1H-indol-3-yl](oxo)acetyl]amino}acetic acid;

2-[(2-{1-Benzyl-5-[4-(trifluoromethoxy)phenyl)-1H-indol-3-yl}-2-oxoacetyl)amino]acetic acid; and 2-[(2-{1-Benzyl-5-{3-trifluoromethoxy)phenyl]-1H-indol-3-yl}-2-oxoacetyl)(methyl)amino}acetic acid, or pharmaceutically acceptable salt or ester forms thereof.

This invention further comprises a method for inhibiting in a mammal plasminogen activator type 1 (PAI-1) comprising administering to a mammal in need thereof a therapeutically effective amount of a compound of formula I:

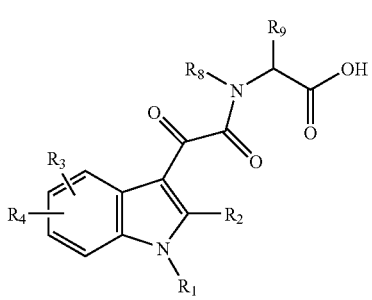

(I)

wherein:

$R_1$ is $C_1$–$C_8$ alkyl, preferably $C_1$–$C_6$ alkyl, $C_3$–$C_6$ cycloalkyl, —$CH_2$—$C_3$—$C_6$ cycloalkyl, pyridinyl, —$CH_2$-pyridinyl, phenyl or benzyl, wherein the rings of the cycloalkyl, pyridinyl, phenyl and benzyl groups may be optionally substituted by 1 to 3 groups selected from the group consisting of halogen, $C_1$–$C_6$ alkyl, $C_1$–$C_3$ perfluoroalkyl, —O—$C_1$—$C_3$ perfluoroalkyl, $C_1$–$C_3$ alkoxy, —OH, —$NH_2$, and —$NO_2$;

$R_2$ is hydrogen, $C_1$–$C_6$ alkyl, $C_3$–$C_6$ cycloalkyl, —$CH_2$— $C_3$—$C_6$ cycloalkyl, or $C_1$–$C_3$ perfluoroalkyl;

$R_3$ is hydrogen, halogen, $C_1$–$C_6$ alkyl, $C_1$–$C_3$ perfluoroalkyl, $C_1$–$C_6$ alkoxy, $C_3$–$C_6$ cycloalkyl, —$CH_2$—$C_3$—$C_6$ cycloalkyl, —$NH_2$, or —$NO_2$;

$R_4$ is phenyl, benzyl, benzyloxy, pyridinyl, or —$CH_2$-pyridinyl, wherein the rings of these groups may be optionally substituted by 1 to 3 groups selected from the group consisting of halogen, $C_1$–$C_3$ alkyl, $C_1$–$C_3$ perfluoroalkyl, —O—$C_1$—$C_3$ perfluoroalkyl, —$C_1$–$C_3$ alkoxy, —OH, —$NH_2$, and —$NO_2$;

$R_8$ is hydrogen, $C_1$–$C_6$ alkyl, $C_3$–$C_6$ cycloalkyl, —$CH_2$— $C_3$—$C_6$ cycloalkyl, or $C_1$–$C_3$ perfluoroalkyl, aryl, substituted aryl, alkyl-aryl, or substituted alkyl-aryl; and $R_9$ is hydrogen, $C_1$–$C_6$ alkyl, $C_3$–$C_6$ branched alkyl, $C_1$–$C_6$ hydroxyalkyl, 4-hydroxybenzyl, 3-indolylmethylene, 4-imidazolylmethylene, $HSCH_2$—, $CH_3SCH_2CH_2$—, $H_2NC(=O)CH_2$—, $H_2NC(=O)CH_2CH_2$—, $HO_2CCH_2$—, $HO_2CCH_2CH_2$—, $H_2NCH_2CH_2CH_2CH_2$—, $H_2NC(=NH)NHCH_2CH_2CH_2$—, or taken together with $R_8$, —$CH_2CH_2CH_2$—;

or a pharmaceutically acceptable salt or ester form thereof.

The preferred salt forms of the compounds herein include but are not limited to sodium salts, and potassium salts. Other useful salt forms of these compounds include those formed with pharmaceutically acceptable inorganic and organic bases known in the art. Salt forms prepared using inorganic bases include hydroxides, carbonates or bicarbonates of the therapeutically acceptable alkali metals or alkaline earth methals, such as sodium potassium, magnesium, calcium and the like. Acceptable organic bases include amines, such as benzylzmine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Also useful are alkylene diamines containing up to 6 carbon atoms, such as hexamethylenediamine; cyclic saturated or unsaturated bases containing up to 6 carbon atoms, including pyrrolidine, peperidine, morpholine, piperazine and their N-alkyl and N-hydroxyalkyl derivatives, such as N-methylmorpholine and N-(2-hyroxyethyl)-piperidine, or pyridine. Quaternary salts may also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-mehtyl-N-(2-hydroxyethyl)-morpholinium, or N,N-dimethyl-piperidinium salt forms. These salt forms may be prepared using the acidic compound(s) of Formula I and procedures known in the art.

Ester forms of the compounds of this invention include straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters. Other esters useful with this invention include those of the formula —$COOR_{10}$ wherein $R_{10}$ is selected from the formulae:

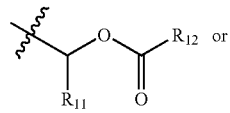

(1)

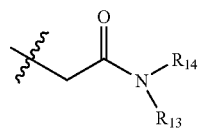

(2)

wherein $R_{11}$, $R_{12}$, $R_{13}$, $R_{14}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Among the preferred ester forms of the compounds herein include but not limited to $C_1$–$C_6$ alkyl esters, $C_3$–$C_6$ branched alkyl esters, benzyl esters, etc.

As used herein, the term alkyl, includes both straight and branched carbon chains. Preferably the $C_1$–$C_3$ perfluoroalkyl substituent is —$CF_3$; the —O—$C_1$—$C_3$ perfluoroalkyl substituent is OC—$_3$; and the —S—$C_1$—$C_3$ perfluoroalkyl substituent is $SCF_3$.

As used herein, "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryl groups include phenyl, naphthyl and the like. As used herein, "heteroaryl" refers to a monocyclic or bicyclic aromatic group of from 1 to carbon atoms and 1 to 4 heteroatoms selected from oxygen, nitrogen and sulfur within at least one ring (if there is more than one ring). Such heteroaryl groups can have a single ring, such as pyridyl, pyrrolyl or furyl groups, or multiple condensed rings, such as indolyl, indolizinyl, benzofuranyl or benzothienyl groups. Preferred heteroaryls include pyridyl, pyrrolyl and furyl.

Unless otherwise limited by the definition for the aryl or heteroaryl groups herein, such groups can optionally be substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Substituents on the alkyl, alkenyl, alkynyl, thioalkoxy and alkoxy groups mentioned above include halogens, CN, OH, and amino groups. Preferred substituents on the aryl groups herein include alkyl, alkoxy, halo, cyano, nitro, trihalomethyl, and thioalkoxy.

The compounds of the present invention are inhibitors of the serine protease inhibitor PAI-1, and are therefore useful in the treatment, inhibition, prevention or prophylaxis in a mammal, preferably in a human, of those processes which involve the production and/or action of PAI-1. Thus, the compounds of the invention are useful in the treatment or prevention of noninsulin dependent diabetes mellitus and cardiovascular disease caused by such condition, and prevention of thrombotic events associated with coronary artery and cerebrovascular disease. These compounds are also useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery (such as joint replacement), and peripheral arterial occlusion. These compounds are also useful in treating stroke associated with or resulting from atrial fibrillation.

The compounds of the invention may also be used in the treatment of diseases associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be used in the treatment of malignancies, and diseases associated with neoangiogenesis (such as diabetic retinopathy).

The compounds of the invention may also be used in conjunction with and following processes or procedures involving maintaining blood vessel patency, including vascular surgery, vascular graft and stent patency, organ, tissue and cell implantation and transplantation.

The compounds in the invention may also be useful in the treatment of inflammatory diseases, septic shock and the vascular damage associated with infections.

The compounds of the invention are useful for the treatment of blood and blood products used in dialysis, blood storage in the fluid phase, especially ex vivo platelet aggregation. The present compounds may also be added to human plasma during the analysis of blood chemistry in hospital settings to determine the fibrinolytic capacity thereof.

The compounds in the present invention may also be used in combination with prothrombolytic, fibrinolytic and anticoagulant agents.

The compounds of the present invention may also be used to treat cancer including, but not limited to, breast and ovarian cancer, and as imaging agents for the identification of metastatic cancers.

The compounds of the invention may also be used in the treatment of Alzheimer's disease. This method may also be characterized as the inhibition of plasminogen activator by PAI-1 in a mammal, particularly a human, experiencing or subject to Alzhemier's disease. This method may also be characterized as a method of increasing or normalizing levels of plasmin concentration in a mammal, particularly those experiencing or subject to Alzheimer's disease.

The compounds of the invention may be used for the treatment of myelofibrosis with myeloid metaplasia by regulating stromal cell hyperplasia and increases in extracellular matrix proteins.

The compounds of the invention may also be used in conjunction with protease inhibitor—containing highly active antiretroviral therapy (HAART) for the treatment of diseases which originate from fibrinolytic impairment and hyper-coagulability of HIV-1 infected patients receiving such therapy.

The compounds of the invention may be used for the treatment of diabetic nephropathy and renal dialysis associated with nephropathy.

The compounds of the invention may be used to treat cancer, septicemia, obesity, insulin resistance, proliferative diseases such as psoriasis, improving coagulation homeostasis, cerebrovascular diseases, microvascular disease, hypertension, dementia, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, reducing the risk of undergoing a myocardial revascularization procedure, microvascular diseases such as nephropathy, neuropathy, retinopathy and nephrotic syndrome, hypertension, Type I and 2 diabetes and related diseases, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/or improving endothelial function, and all forms of cerebrovascular diseases.

The compounds of the invention may be used for the topical applications in wound healing for prevention of scarring.

Methods for the treatment, inhibition, prevention or prophylaxis in a mammal of each of the conditions or maladies listed herein are part of the present invention. Each method comprises administering to a mammal in need thereof a pharmaceutically or therapeutically effective amount of a compound of this invention, or a pharmaceutically acceptable salt or ester form thereof.

This invention also provides pharmaceutical compositions comprising a pharmaceutically or therapeutically effective amount of a compound of this invention, or a pharmaceutically acceptable salt or ester form thereof, either alone or in combination with one or more pharmaceutically acceptable carriers or excipients (i.e. pharmaceutically acceptable materials with no pharmacological effects). It will be understood that a pharmaceutically or therapeutically effective amount of a compound herein refers to an amount of the compound in question which will sufficiently inhibit the serine protease inhibitor PAI-1in the mammal in need thereof to a sufficient extent to provide a desirable improvement in the condition in question or provide sufficient inhibition of the serine protease inhibitor PAI-1 to prevent, inhibit or limit the onset of the physiological basis for the malady or condition in question.

PROCESS OF THE INVENTION

The compounds of the present invention can be readily prepared according to the method described in following reaction scheme or a modification thereof, which will be recognized by one skilled in the art using readily available starting materials, reagents and conventional synthetic procedures. It is also possible to make use of variants of these process steps, which in themselves are known to and well within the preparatory skill of the medicinal chemist. In the following reaction schemes, R, $R_1$, $R_2$, $R_3$, $R_4$, $R_5$, $R_6$, $R_7$, $R_8$ and $R_9$ are selected from the groups defined above.

The bromo-indoles (II) were either commercially available or were prepared following known literature procedures (e.g., Ayer et.al, *Tetrahedron Letters*, 48 (14) 2919–2924, 1992; Rapoport et.al, *JOC*, 51, 5106–5110, 1986).

In Scheme I, the bromo-indoles (II) were reacted with alkyl halides or aryl-alkyl halides using a base such as sodium hydride in DMF or THF to give the N-substituted bromo-indoles (III). The N-substituted bromo-indoles (III) were converted to the corresponding boronic acids (IV) by treating III in THF with nBuLi, followed by triisopropylborate and subsequent quenching with aqueous acid. Boronic acids (IV) were then subjected to palladium catalyzed cross-coupling with various substituted aryl-halides affording the aryl-indoles (VI). Alternatively, N-substituted bromo-indoles (III) were subjected to the palladium catalyzed cross-coupling with various substituted aryl-boronic acids to afford the aryl-indoles (VI). Furthermore, reaction of bromo-indoles (II) with various substituted aryl-boronic acids under the palladium catalyzed cross-coupling conditions afforded the aryl-indoles (V). Alkylation of (V) with alkyl-halides or aryl-alkyl-halides under basic conditions as described above afforded the N-substituted aryl-indoles (VI). Reaction of VI with oxalyl chloride in methylene chloride followed by quenching with N-substituted amino acid esters afforded the oxo-acetyl amino acetate (IX). Alternatively ketoacids (VIII) are converted to the oxo-acetyl amino acetate (IX) by coupling with N-substituted amino acid esters in presence of HOBT, a base such as triethyl amine, and a carbodiimide such as DCC, in a solvent such as dichloromethane. Base hydrolysis of the acetate (IX) followed by acidification afforded the desired compounds (I). The ketoacids (VIII) are prepared by reaction of VI with oxalyl chloride in methylene chloride followed by quenching with water. Alternatively reaction of VI with oxalyl chloride in methylene chloride followed by quenching with alcohol afforded the keto-esters (VII). The ketoesters (VII) can be purified by either crystallization or chromatography. Conversion of the ketoesters (VII) to the corresponding ketoacids (VII) was accomplished by saponification of the ester followed by neutralization with an acid such as hydrochloric acid.

Scheme I

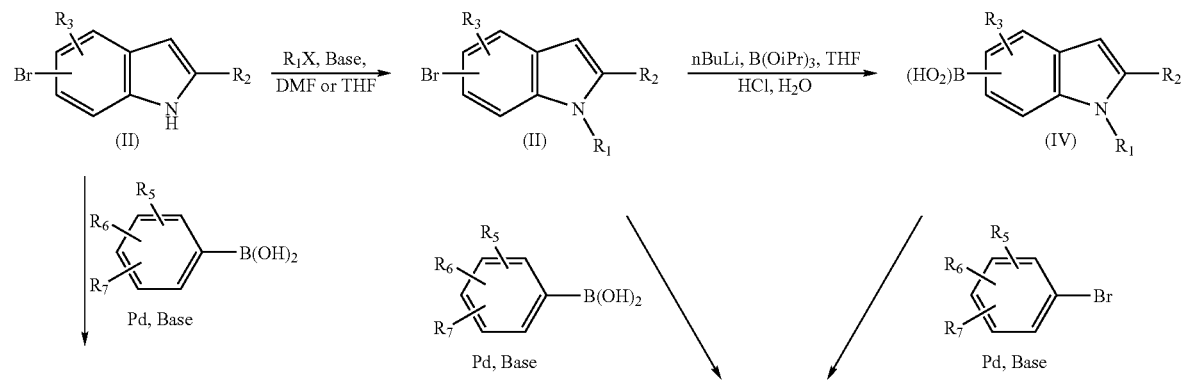

-continued

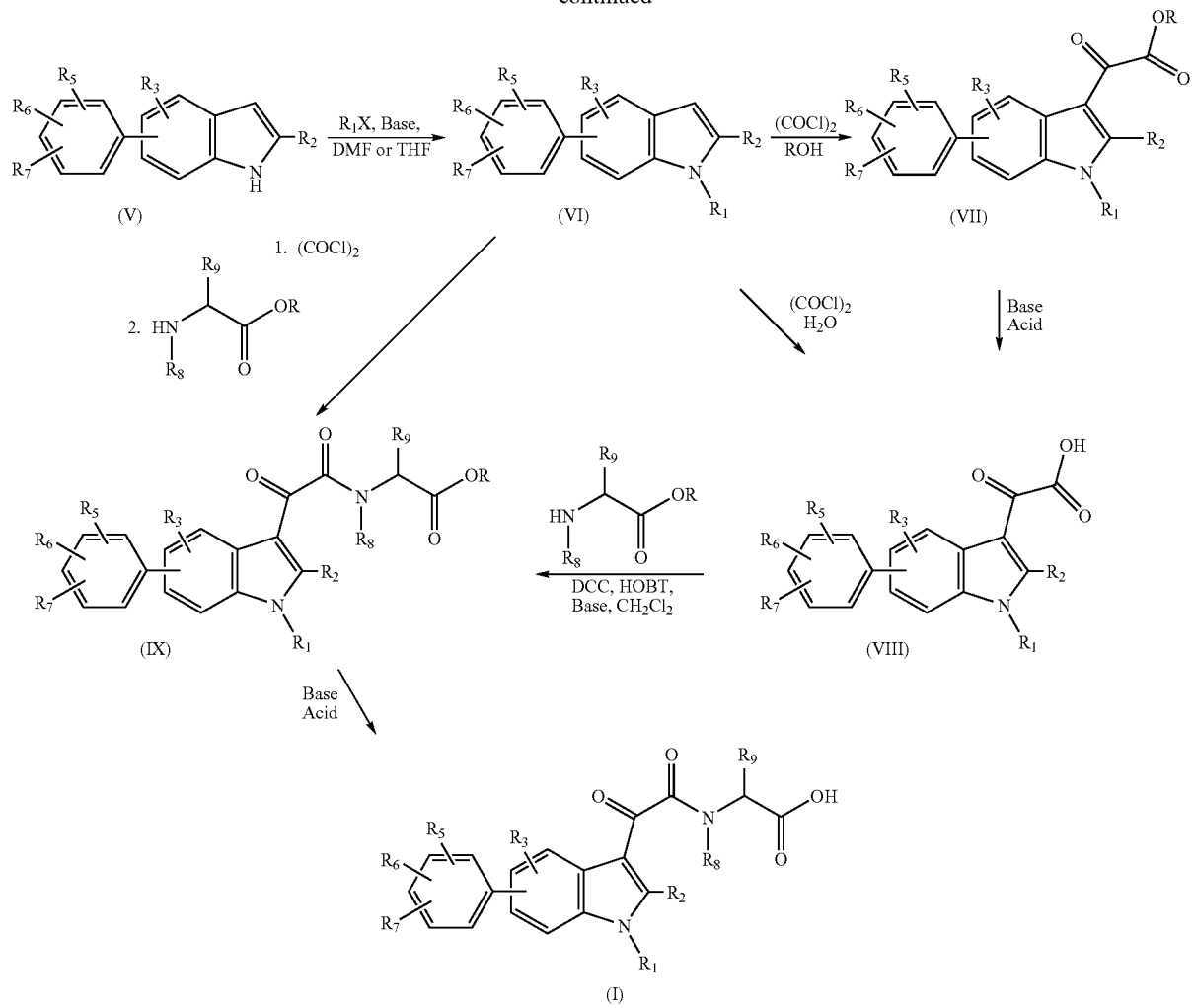

The present invention also provides pharmaceutical compositions comprising the indole oxo-acetylamino acetic acid derivatives of formula (I) either alone or in combination with excipients (i.e. pharmaceutically acceptable materials with no pharmacological effects). Such compositions for treating conditions resulting from fibrinolytic disorder such as deep vein thrombosis and coronary heart disease, pulmonary fibrosis, etc.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid, which is in admixture with the finely divided active ingredient. In tablets, the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of PAI-1 and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

Primary Screen for the PAI-1 Inhibition

The ability of the compounds of this invention to inhibit plasminogen activator inhibitor-1 was established by the following experimental procedures:

Test compounds were dissolved in DMSO at a final concentration of 10 mM, then diluted 100× in physiologic buffer. The inhibitory assay was initiated by the addition of the test compound (1–100 µM final concentration, maximum DMSO concentration of 0.2%) in a pH 6.6 buffer containing 140 nM recombinant human plasminogen activator inhibitor-1 (Molecular Innovations, Royal Oak, Mich.). Following a 1 hour incubation at room temperature, 70 nM of recombinant human tissue plasminogen activator (tPA) was added, and the combination of the test compound, PAI-1 and tPA was incubated for an additional 30 minutes. Following the second incubation, Spectrozyme-tPA (American Diagnostica, Greenwich, Conn.), a chromogenic substrate for tPA, was added and absorbance was read at 405 nm at 0 and 60 minutes. Relative PAI-1 inhibition was equal to the residual tPA activity in the presence of the test compounds and PAI-1. Control treatments included the complete inhibition of tPA by PAI-1 at the molar ratio employed (2:1), and the absence of any effect of the test compound on tPA alone.

Assay for Determining $IC_{50}$ of Inhibition of PAI-1

This assay was based upon the non-SDS dissociable interaction between tPA and active PAI-1. Assay plates were initially coated with human tPA (10 µg/ml). Test compounds were dissolved in DMSO at 10 mM, then diluted with physiologic buffer (pH 7.5) to a final concentration of 1–50 µM. The test compounds were incubated with human PAI-1 (50 ng/ml) for 15 minutes at room temperature. The tPA-coated plate was washed with a solution of 0.05% Tween 20 and 0.1% BSA, then the plate is blocked with a solution of 3% BSA. An aliquot of the test compound/PAI-1 solution was then added to the tPA-coated plate, incubated at room temperature for 1 hour, and washed. Active PAI-1 bound to the plate was assessed by adding an aliquot of a 1:1000 dilution of the 33B8 monoclonal antibody against human PAI-1, and incubating the plate at room temperature for 1 hour (Molecular Innovations, Royal Oak, Mich.). The plate was again washed, and a solution of goat anti-mouse IgG-alkaline phosphatase conjugate was added at a 1:50,000 dilution in goat serum. The plate was incubated 30 minutes at room temperature, washed, and a solution of alkaline phosphatase substrate was added. The plate was incubated 45 minutes at room temperature, and color development is determined at $OD_{405nm}$. The quantitation of active PAI-1 bound to tPA at varying concentrations of the test compound was used to determine the $IC_{50}$. Results were analyzed using a logarithmic best-fit equation. The assay sensitivity is 5 ng/ml of human PAI-1 as determined from a standard curve ranging from 0–100 ng/ml.

The compounds of the present invention inhibited Plasminogen Activator Inhibitor-1 as summarized in Table I.

TABLE I

| Example | $IC_{50}$ (uM) | % Inhibition @ 25 uM |
|---------|----------------|----------------------|
| 1       | 29             |                      |
| 2       | 28             |                      |
| 3       | —              | 24                   |

EXAMPLE 1

{[[1-(4-tert-butylbenzyl)-5-(3-methylphenyl)-1H-indol-3-yl](oxo)acetyl]amino}acetic acid Step 1

5-Bromo-1-[4-(tert-butyl)benzyl]-1H-indole

NaH (60%, 36.8 g, 921 mmol) was added portionwise to a stirring solution of 5-bromoindole (152.0 g, 768 mmol) in DMF (1.4 L) at 0° C. under a nitrogen atmosphere over a period of one hour. The mixture was stirred at 0° C. for one hour and at room temperature for 2.5 hours. 4-(tert-Butyl) benzyl bromide (180.0 g, 768 mmol) was added over a period of one hour. The mixture was stirred at room temperature for 3 hours. The reaction was quenched with aqueous ammonium chloride (5%, 1.4 L). The precipitated solid was isolated by filtration, washed with water (5×0.5 L), then with petroleum ether (0.3 L). The solid was dried in the air and then under vacuum at 60° C. for 18 hours to afford the title compound as a white solid (257 g, 97%), m.p. 108–109° C. Mass spectrum (ESI, [M+H]$^+$) m/z 342. $^1$HNMR (400 MHz, DMSO-d$_6$) δ 7.73 (s, 1H), δ 7.55 (s, 1H), δ 7.44 (d, 1H, J=8.71 Hz), 7.30 (d, 2H, J=7.96 Hz), 7.19 (d, 1H, J=8.71 Hz), 7.10 (d, 2H, J=7.63 Hz), 6.46 (s, 1H), 5.36 (s, 2H), and 1.21 ppm (s, 9H).

Elemental Analysis for $C_{19}H_{20}BrN$: Calculated: C, 66.67; H, 5.89; N, 4.09. Found: C, 66.78; H, 5.86; N, 4.02.

Step 2

1-[4-(tert-Butyl)benzyl]-5-(3-methylphenyl)-1H-indole

The mixture of 5-bromo-1-(4-tert-butylbenzyl)-1H-indole (67.5 g, 197.2 mmol), 3-methylbenzeneboronic acid (27.6 g, 197.2 mmol), potassium carbonate (27.2 g, 493 mmol), palladium(II) acetate (0.338 g) and tetrabutylammonium bromide (63.5 g, 197.2 mmol) in 10% dioxane in water (degassed, 1.72 L) was stirred at 70° C. The reaction was monitored by TLC. 3-Methylbenzeneboronic acid (45.2 g, 394.4 mmol) was added in four portions every 10 hours, after which time 5-bromo-1-(4-tert-butylbenzyl)-1H-indole was no longer detected by TLC. The reaction was cooled to room temperature and the solvent was decanted. The dark gum-like oil was washed with water and extracted with petroleum ether (4×2 L). The combined petroleum ether extracts were washed with water and filtered. This filtrate was concentrated to a volume of about 1.5 L and allowed to crystallize. The solid was isolated by filtration and dried under vacuum at 60° C. for 10 hours to afford the title compound as a white solid (50.8 g, 73%), mp: 94–95° C. Mass spectrum (ESI, [M+H]$^+$) m/z 354. $^1$HNMR (400 MHz, DMSO-d$_6$): δ 7.79 (s, 1H), 7.53–7.51 (m, 2H), 7.45 (s, 1H), 7.41 (d, 1H, J=7.79 Hz), 7.37 (d, 2H, J=8.55 Hz), 7.32–7.28 (m, 3H), 7.14 (d, 2H, J=8.40 Hz), 7.09 (d, 1H, J=8.40 Hz), 6.51 (d, 1H, J=2.75 Hz), 5.38 (s, 2H), 2.36 (s, 3H), and 1.21 ppm (s, 9H).

Elemental Analysis for $C_{26}H_{27}N$: Calculated: C, 88.34; H, 7.70; N, 3.96. Found: C, 88.24; H, 7.64; N, 3.92.

Step 3

[1-[4-(tert-Butyl)benzyl]-5-(3-methylphenyl)-1H-indol-3-yl](oxo)acetyl]amino}acetic acid Oxalyl chloride (0.074 mL, 0.85 mmol) was added dropwise to a stirring solution of 1-[4-(tert-butyl)benzyl]-5-(3-methylphenyl)-1H-indone (0.15 g, 0.424 mmol) in THF (4.5 mL) at room temperature over a period of 5 minutes under a nitrogen atmosphere. After the reaction mixture was stirred at room temperature for 4 hours, the a solution of glycine (0.143 mg, 1.91 mmol) in DMF (4.5 mL) was added slowly and the mixture was stirred at room temperature overnight. The reaction was quenched with water and the mixture was extracted with ethyl acetate. The organic extract was washed with water, and brine then concentrated to give an oil. This oil was purified by flash chromatography using dichloromethane/methanol (9:1) as an eluant to give the title compound as a light brown solid (0.138 g, 67%), mp: 120–121° C. Mass spectrum (ESI, [M+H]$^+$) m/z 483. $^1$HNMR (400 MHz, DMSO-d$_6$): δ 12.70 (b, 1H), 9.03 (s, 1H), 8.95 (t, 1H), 8.47 (s, 1H), 7.70 (d, 1H, J=8.55 Hz), 7.56 (dd, 1H, J=8.55 and 1.68 Hz), 7.46 (s, 1H), 7.43 (d, 1H, J=8.10 Hz), 7.40–7.34 (m, 3H), 7.25 (d, 2H, J=8.40 Hz), 7.16 (d, 1H, J=7.48 Hz), 5.57 (s, 2H), 3.91 (d, 2H), 2.39 (s, 3H), and 1.22 ppm (s, 9H).

Elemental Analysis for $C_{30}H_{30}N_2O_4$. ○0.2 H$_2$O: Calculated: C, 74.11; H, 6.30; N, 5.76. Found: C, 73.90; H, 6.00; N, 5.50.

EXAMPLE 2

2-[(2-{1-Benzyl-5-[4-(trifluoromethoxy)phenyl]-1H-indol-3-yl}-2-oxoacetyl)amino]acetic acid Step 1

1-Benzyl-5-bromo-1H-indole

A solution of 5-bromoindole (5.02 g, 25.6 mmol) in DMF (50 mL) was cooled in an ice bath. Sodium hydride (2.30 g of 60% dispersion in oil, 57.5 mmol) was added. After stirring for 40 minutes under nitrogen at room temperature, the reaction mixture was again cooled in an ice bath and benzyl bromide (6.7 mL, 56 mmol) was added. The reaction mixture was stirred for 2 hours, poured into excess water, acidified with 2N hydrochloric acid and extracted with ethyl acetate. The organic phase was washed with water and brine, dried over anhydrous magnesium sulfate and evaporated to dryness. The residue was purified by flash chromatography (Biotage apparatus) using hexane as an eluant. Dyring at 60° C. for 35 minutes yielded the title compound as a white solid (5.69 g, 78%), mp 93–95° C. Mass spectrum (+ESI, [M+H]$^+$) m/z 286; $^1$HNMR (500 MHz, DMSO-d$_6$): δ7.7 (d,1H, J=1.8 Hz), 7.55 (d, 1H, J=3.1 Hz), 7.4 (d, 1H, J=8.7 Hz), 7.15–7.30 (m, 6H), 6.45 (dd, 1H, J=3.2 Hz and 0.6 Hz), and 5.45 ppm (s, 2H).

Elemental Analysis for $C_{15}H_{12}BrN$: Calcd: C, 62.96; H, 4.23; N, 4.89; Found: C, 63.36; H, 4.31; N, 4.73.

Step 2

1-Benzyl-5-[4-(trifluoromethoxy)phenyl]-1H-indole

A mixture of 1-benzyl-5-bromo-1H-indole (5.2 g, 18 mmol), 4-trifluoromethoxyphenylboronic acid (4.7 g, 23 mmol), [1,1'-bis(diphenylphosphino)ferrocene]dichloropalladium (II) complex with dichloromethane (1:1) (0.88 g, 1.1 mmol), potassium carbonate (3.8 g, 27 mmol) in dioxane (135 mL) and water (13.5 mL) was heated at 77° C. for 5 hours. The reaction mixture was evaporated to dryness and partitioned in ethyl acetate and 2N hydrochloric acid. The organic phase was washed with water and brine, dried over anhydrous anhydrous magnesium sulfate, filtered and evaporated to dryness. The residue was purified by flash chromatography (Biotage apparatus) using hexane as an eluant to yield the title compound as a light yellow wax/solid (2.8 g, 42%), mp 62–63° C. $^1$HNMR (300 MHz, DMSO-d$_6$): δ7.85 (s, 1H), 7.75 (d, 2H, J=7.7 Hz), 7.5–7.6 (m, 2H), 7.4 (d, 3H, J=7.7 Hz), 7.2-7.35 (m, 5H), 6.6 (d, 1H, J=3.9 Hz), and 5.45 ppm (s, 2H).

Step 3

Ethyl 2-{1-benzyl-5-[4-(trifluoromethoxy)phenyl]-1H-indol-3-yl}-2-oxoacetate

To a solution of 1-benzyl-5-[4-(trifluoromethoxy)phenyl]-1H-indole (2.80 g, 7.62 mmol) in dry THF (40 mL) under nitrogen at 0° C. was added oxalyl chloride (2.0 mL, 23 mmol). The reaction mixture was stirred for one hour. It was cooled in an ice bath and ethanol (4.5 mL) was added. The reaction mixture was stirred for 25 minutes at room temperature then poured into excess aqueous sodium bicarbonate solution and extracted with ethyl acetate. The organic phase was washed with water and brine, dried over anhydrous magnesium sulfate, and evaporated to dryness. The residue was purified by flash chromatography using 5–10% ethyl acetate in hexane as an eluant. Drying for 35 minutes at 60° C. yielded the title compound as a yellow gum (3.05 g, 86%): $^1$HNMR (300 MHz, DMSO-d$_6$): δ8.75 (s, 1H), 8.45 (s, 1H), 7.8 (d, 2H, J=9.2 Hz), 7.75 (d, 1H, J=9.2 Hz), 7.6 (d, 1H, J=9.2 Hz), 7.45 (d, 2H, J=9.2 Hz), 7.3–7.4 (m, 5H), 5.85 (s, 2H), 4.35 (q, 2H, J=7.5 Hz), and 1.35 ppm (t, 3H, J=7.5 Hz).

Step 4

2-{1-Benzyl-5-[4-(trifluoromethoxy)phenyl]-1H-indol-3-yl}-2-oxoacetic acid

A mixture of ethyl 2-{1-benzyl-5-[4-(trifluoromethoxy)phenyl]-1H-indol-3-yl}-2-oxoacetate(0.463 g, 0.991 mmol), potassium hydroxide (0.224 g, 3.99 mmol) in THF (5 mL) and water (5 mL) was stirred for 40 minutes at room temperature then poured into excess water, acidified with 2N hydrochloric acid and extracted with ethyl acetate. The organic phase was washed with water and brine, dried over anhydrous magnesium sulfate, and evaporated to dryness. The residue was dried for 15 hours at 80° C. to yield the title compound as a light yellow solid (0.314 g, 78%), mp 169–171° C. A sample was crystallized from acetonitrile for analysis. Mass spectrum (+APCI, [M+H]$^+$) m/z 440; $^1$HNMR (400 MHz, DMSO-d$_6$): δ13.8–14.2 (br,1H), 8.75 (s, 1H), 8.45 (d, 1H, J=1.5 Hz), 7.75–7.8 (m, 2H), 7.7 (d, 1H, J=8.5 Hz), 7.6 (dd, 1H, J=8.7 Hz), 7.45 (d, 2H, J=8.8 Hz), 7.25–7.35 (m, 5H), and 5.65 ppm (s, 2H).

Elemental Analysis for $C_{24}H_{16}F_3NO_4$: Calcd: C, 65.61; H, 3.67; N, 3.19. Found: C, 65.59; H, 3.54; N, 3.17.

Step 5 tert-Butyl 2-[(2-{1-benzyl-5-[4-(trifluoromethoxy)phenyl]-1H-indol-3-yl}-2-oxoacetyl)amino]acetate To an ice-cooled solution of 2-{1-benzyl-5-[4-(trifluoromethoxy)phenyl]-1H-indol-3-yl}-2-oxoacetic acid (1.47 g, 3.35 mmol) in methylene chloride (25 mL) was added 1-hydroxybenzotriazole hydrate (0.771 g, 5.03 mmol). The reaction mixture was stirred for few minutes in an ice bath. Triethylamine (0.47 mL, 3.4 mmol), and glycine tert-butyl ester hydrochloride (0.573 g, 3.42 mmol) were added. After stirring for five more minutes in the ice bath, dicyclohexylcarbodiimide (0.88 g, 4.27 mmol) was added. The reaction mixture was then stirred at room temperature for 2 hours under nitrogen. The mixture was filtered. The insoluble matter was washed with ethyl acetate. The combined filtrate was evaporated to dryness. The residue was partitioned in ethyl acetate and 2N hydrochloric acid. The organic phase was washed with brine and evaporated to dryness. The residue was purified by flash chromatography (Biotage apparatus) using 2.5–12.5% ethyl acetate in hexane to yield the title compound as a yellow solid (1.47 g, 80%), mp 167–168° C. Mass spectrum (–ESI, [M-H]$^-$) m/z 551.7; $^1$HNMR (500 MHz, DMSO-d$_6$): δ9.05 (s, 1H), 9.0 (t, 1H, J=6.0 Hz), 8.5 (d, 1H, J=1.5 Hz), 7.75–7.8 (m, 2H), 7.7 (d, 1H, J=8.4 Hz), 7.6 (dd, 1H, J=8.6 Hz and 1.8 Hz), 7.45 (d, 1H, J=8.1 Hz), 7.3–7.35 (m, 5H), 5.65 ppm (s, 2H), 3.9 (d, 2H, J=6.1 Hz), and 1.45 ppm (s, 9H).

Step 6

2-[(2-{1-Benzyl-5-[4-(trifluoromethoxy)phenyl]-1H-indol-3-yl}-2-oxoacetyl)amino]acetic acid To an ice-cooled solution of tert-butyl 2-[(2-{1-benzyl-5-[4-(trifluoromethoxy)phenyl]-1H-indol-3-yl}-2-oxoacetyl)amino]acetate (1.33 g, 2.41 mmol) in methylene chloride (25 mL) was added 12 mL (160 mmol) of trifluoroacetic acid. The reaction mixture was stirred for two hours at room temperature then concentrated. The residue was crystallized twice from isopropanol. It was dried for 15 hours at 95° C. to give the title compound as yellow solid (0.928 g, 77%), mp 211–2° C. (dec.). Mass spectrum (–ESI, [M-H]$^-$) m/z 495; $^1$HNMR (500 MHz, DMSO-d$_6$): δ12.5–13.0 (br,1H), 9.05 (s, 1H), 8.95 (t, 1H, J=6.1 Hz), 8.5 (d, 1H, J=1.5 Hz), 7.75–7.8 (m, 2H), 7.7 (d, 1H, J=8.6 Hz), 7.6 (dd, 1H, J=8.6 Hz and 1.8 Hz), 7.45 (d, 2H, J=8.1 Hz), 7.25–7.35 (m, 5H), 5.65 (s, 2H), and 3.9 ppm (d, 2H, J=6.1 Hz).

Elemental Analysis for $C_{26}H_{19}F_3N_2O_5$: Calcd: C, 62.90; H, 3.86; N, 5.64. Found: C, 62.93; H, 3.78; N, 5.38.

EXAMPLE 3

2-[(2-{1-Benzyl-5-[3-(trifluoromethoxy)phenyl]-1H-indol-3-yl}-2-oxoacetyl)(methyl)amino]acetic acid Step 1 tert-Butyl 2-[(2-{1-benzyl-5-[3-(trifluoromethoxy)phenyl]-1H-indol-3-yl}-2-oxoacetyl)(methyl)amino]acetate To an ice-cooled solution of 2-{1-benzyl-5-[4-(trifluoromethoxy)phenyl]-1H-indol-3-yl}-2-oxoacetic acid (Step 4 of Example 2) (4.59 g, 10.4 mmol) in methylene chloride (100 mL) was added 1-hydroxybenzotriazole hydrate (2.44 g, 15.9 mmol). The reaction mixture was stirred for 5 minutes while cooling. Triethylamine (1.5 mL, 11 mmol), and sarcocine tert-butyl ester hydrochloride (1.94 g, 10.7 mmol) were added. After stirring for five more minutes in the ice bath, dicyclohexylcarbodiimide (2.78 g, 13.5 mmol) was added. The reaction mixture was then stirred for 3 hours under nitrogen at room temperature. The reaction was worked up as described in Step 5 of Example 1. Purification by flash chromatography using 10–50% ethyl acetate in hexane yielded the title compound as a light peach foam/gum (5.21 g, 88%); $^1$HNMR (400 MHz, DMSO-d$_6$): δ8.35–8.4 (m, 2H), 7.7–7.75 (m, 3H), 7.5–7.6 (m, 1H), 7.4–7.45 (m, 2H), 7.25–7.35 (m, 5H), 5.55 (d, 2H, J=3.0 Hz), 4.1 (d, 2H, J=12.3 Hz), 3.0 (d, 3H, J=25.4 Hz), 1.4 (s, 6H), and 1.2 ppm (s, 3H).

Step 2

2-[(2-{1-benzyl-5-[3-(trifluoromethoxy)phenyl]-1H-indol-3-yl}-2-oxoacetyl)(methyl)amino]acetic acid To an ice-cooled solution of tert-butyl 2-[(2-{1-benzyl-5-[3-(trifluoromethoxy)phenyl]-1H-indol-3-yl}-2-oxoacetyl)(methyl)amino]acetate (5.17 g, 9.13 mmol) in methylene chloride (60 mL) was added trifluoroacetic acid (30 mL, 390 mmol). The reaction mixture was stirred for 1.5 hours at room temperature and concentrated. The residue was treated with diethyl ether and the mixture was concentrated to the precipitation point. The solid was purified by HPLC using 70% acetonitrile/0.1% formic acid in water as the mobile phase. The acetonitrile was evaporated, and the aqueous phase was extracted with ethyl acetate and washed with water and brine. The organic phase was evaporated to dryness and the residue was dried for 15 hours at 91° C. to give the title compound as a light pink solid (2.81 g, 60%), mp 178–179° C. Mass spectrum (–ESI, [M-H]$^-$) m/z 509; $^1$HNMR (500 MHz, DMSO-d$_6$): δ12.8–13.2 (br,1H), 8.45 (m, 1H), 8.35 (d, 1H, J=8.4 Hz), 7.7–7.8 (m, 3H), 7.55–7.65 (m, 2H), 7.4–7.45 (m, 2H), 7.25–7.35 (m, 5H), 5.6 (d, 2H, J=3.5 Hz), 4.15 (d, 2H, J=21.0 Hz), and 3.0 ppm (dd, 3H, J=22.0 Hz and 0.78 Hz).

Elemental Analysis for $C_{27}H_{21}F_3N_2O_5+0.2H_2O$: Calcd: C, 63.08; H, 4.20; N, 5.45. Found: C, 63.02; H, 4.13; N, 5.20.

What is claimed:

1. A compound of formula I:

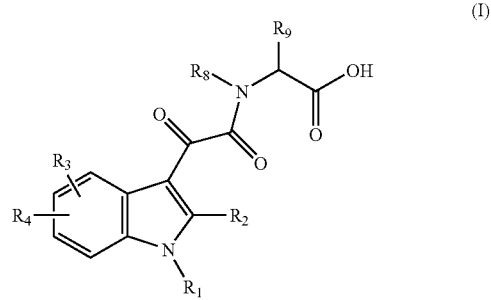

wherein:
R$_1$ is C$_1$–C$_8$ alkyl, C$_3$–C$_6$ cycloalkyl, —CH$_2$—C$_3$–C$_6$ cycloalkyl, pyridinyl, —CH$_2$-pyridinyl, phenyl or benzyl, the rings of the cycloalkyl, pyridinyl, phenyl and benzyl groups are optionally substituted by from 1 to 3 groups selected from the group consisting of halogen, C$_1$–C$_6$ alkyl, C$_1$–C$_3$ perfluoroalkyl, —O—C$_1$–C$_3$ perfluoroalkyl, C$_1$–C$_3$ alkoxy, —OH, —NH$_2$, and —NO$_2$;

$R_2$ is hydrogen, $C_1$–$C_6$ alkyl, $C_3$–$C_6$ cycloalkyl, —$CH_2$—$C_3$–$C_6$ cycloalkyl, or $C_1$–$C_3$ perfluoroalkyl;

$R_3$ is hydrogen, halogen, $C_1$–$C_6$ alkyl, $C_1$–$C_3$ perfluoroalkyl, $C_1$–$C_6$ alkoxy, $C_3$–$C_6$ cycloalkyl, —$CH_2$—$C_3$–$C_6$ cycloalkyl, —$NH_2$, or —$NO_2$;

$R_4$ is phenyl, benzyl, benzyloxy, pyridinyl, or —$CH_2$-pyridinyl, wherein the rings of these groups are optionally substituted by 1 to 3 groups selected from the group consisting of halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, and —$NO_2$;

$R_8$ is hydrogen, $C_1$–$C_6$ alkyl, $C_3$–$C_6$ cycloalkyl, —$CH_2$—$C_3$–$C_6$ cycloalkyl, $C_1$–$C_3$ perfluoroalkyl, aryl, substituted aryl, alkyl-aryl, or substituted alkyl-aryl; and $R_9$ is hydrogen, $C_1$–$C_6$ alkyl, $C_3$–$C_6$ branched alkyl, 4-hydroxybenzyl, 3-indolylymethylene, 4-imidazolylmethylene, $CH_3SCH_2CH_2$—, $H_2NC(=O)CH_2$—, $H_2NC(=O)CH_2CH_2$—, $HO_2CCH_2$—, $HO_2CCH_2CH_2$—, $H_2NCH_2CH_2CH_2CH_2$—, $H_2NC(=NH)NHCH_2CH_2CH_2$—, or taken together with $R_8$, —$CH_2CH_2CH_2$—;

or a pharmaceutically acceptable salt or ester form thereof.

2. A compound of claim 1 having the formulas:

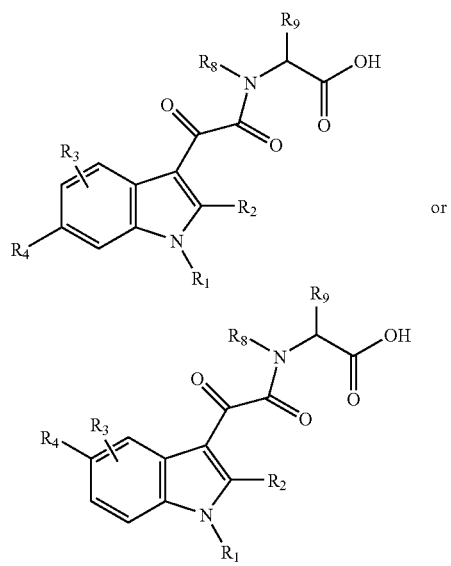

wherein $R_1$, $R_2$, $R_3$, $R_4$, $R_8$ and $R_9$ are as defined in claim 1, or a pharmaceutically acceptable salt or ester form thereof.

3. A compound of claim 1 having the formulas:

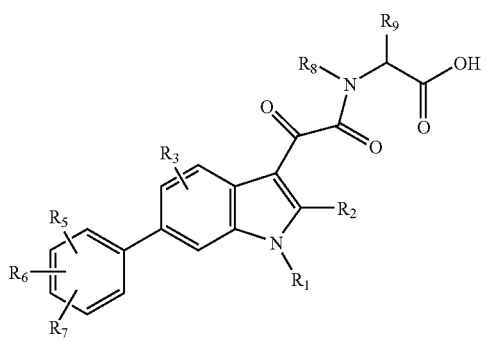

-continued

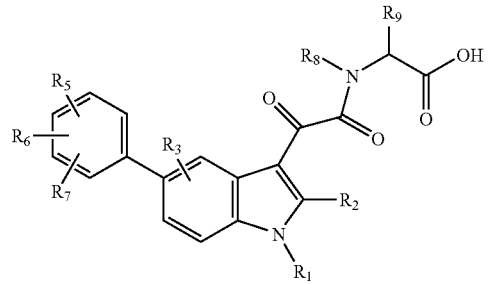

wherein:

$R_1$ is $C_1$–$C_8$ alkyl, $C_3$–$C_6$ cycloalkyl, —$CH_2$—$C_3$–$C_6$ cycloalkyl, or benzyl, wherein the rings of the cycloalkyl and benzyl groups are optionally substituted by from 1 to 3 groups selected from halogen, $C_1$–$C_3$ alkyl, $C_1$–$C_3$ perfluoroalkyl, —O—$C_1$–$C_3$ perfluoroalkyl, preferably —O—$CF_3$, $C_1$–$C_3$ alkoxy, —OH, —$NH_2$, or —$NO_2$;

$R_2$ is hydrogen, $C_1$–$C_6$ alkyl, $C_3$–$C_6$ cycloalkyl, —$CH_2$—$C_3$–$C_6$ cycloalkyl, or $C_1$–$C_3$ perfluoroalkyl;

$R_3$ is hydrogen, halogen, $C_1$–$C_6$ alkyl, $C_1$–$C_3$ perfluoroalkyl, $C_1$–$C_6$ alkoxy, $C_3$–$C_6$ cycloalkyl, —$CH_2$—$C_3$–$C_6$ cycloalkyl, —$NH_2$, or —$NO_2$;

$R_5$, $R_6$ and $R_7$ are each independently hydrogen, halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, or —$NO_2$;

$R_8$ is hydrogen, $C_1$–$C_6$ alkyl, $C_3$–$C_6$ cycloalkyl, —$CH_2$—$C_3$–$C_6$ cycloalkyl, $C_1$–$C_3$ perfluoroalkyl, aryl, substituted aryl, alkyl-aryl, or substituted alkyl-aryl;

$R_9$ is hydrogen, $C_1$–$C_6$ alkyl, $C_3$–$C_6$ branched alkyl, 4-hydroxybenzyl, 3-indolylymethylene, 4-imidazolylmethylene, $CH_3SCH_2CH_2$—, $H_2NC(=O)CH_2$—, $H_2NC(=O)CH_2CH_2$—, $HO_2CCH_2$—, $HO_2CCH_2CH_2$—, $H_2NCH_2CH_2CH_2CH_2$—, $H_2NC(=NH)NHCH_2CH_2CH_2$—, or taken together with $R_8$, —$CH_2CH_2CH_2$—;

or a pharmaceutically acceptable salt or ester form thereof.

4. The compound of claim 1 which is {[[1-(4-tert-butylbenzyl)-5-(3-methylphenyl) -1H-indol-3-yl](oxo)acetyl]amino}acetic acid, or a pharmaceutically acceptable salt or ester form thereof.

5. The compound of claim 1 which is 2-[(2-{1-Benzyl-5-[4-(trifluoromethoxy) phenyl]-1H-indol-3-yl}-2-oxoacetyl)amino]acetic acid, or a pharmaceutically acceptable salt or ester form thereof.

6. The compound of claim 1 which is 2-[(2-{1-Benzyl-5-[3-(trifluoromethoxy)phenyl]-1H-indol-3-yl}-2-oxoacetyl)(methyl)amino]acetic acid, or a pharmaceutically acceptable salt or ester form thereof.

7. A method of inhibiting plasminogen activator inhibitor-1 in a mammal, for treatment of thrombosis or fibrinolytic impairment in a mammal, wherein the thrombosis or fibrinolytic impairment is associated with formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery or peripheral arterial occlusion, comprising administering to a mammal in need thereof a pharmaceutically effective amount of compound of formula:

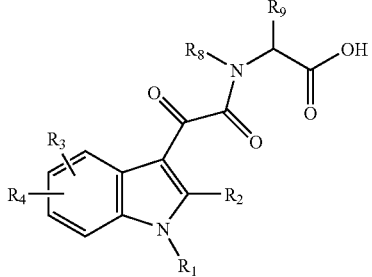

wherein:
- $R_1$ is $C_1$–$C_8$ alkyl, $C_3$–$C_6$ cycloalkyl, —$CH_2$—$C_3$–$C_6$ cycloalkyl, pyridinyl, —$CH_2$-pyridinyl, phenyl or benzyl, the rings of the cycloalkyl, pyridinyl, phenyl and benzyl groups are optionally substituted by from 1 to 3 groups selected from the group consisting of halogen, $C_1$–$C_6$ alkyl, $C_1$–$C_3$ perfluoroalkyl, —O—$C_1$–$C_3$ perfluoroalkyl, $C_1$–$C_3$ alkoxy, —OH, —$NH_2$, and —$NO_2$;
- $R_2$ is hydrogen, $C_1$–$C_6$ alkyl, $C_3$–$C_6$ cycloalkyl, —$CH_2$—$C_3$–$C_6$ cycloalkyl, or $C_1$–$C_3$ perfluoroalkyl;
- $R_3$ is hydrogen, halogen, $C_1$–$C_6$ alkyl, $C_1$–$C_3$ perfluoroalkyl, $C_1$–$C_6$ alkoxy, $C_3$–$C_6$ cycloalkyl, —$CH_2$—$C_3$–$C_6$ cycloalkyl, —$NH_2$, or —$NO_2$;
- $R_4$ is phenyl, benzyl, benzyloxy, pyridinyl, or —$CH_2$-pyridinyl, wherein the rings of these groups are optionally substituted by 1 to 3 groups selected from the group consisting of halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —$NH_2$, and —$NO_2$;
- $R_8$ is hydrogen, $C_1$–$C_6$ alkyl, $C_3$–$C_6$ cycloalkyl, —$CH_2$—$C_3$–$C_6$ cycloalkyl, $C_1$–$C_3$ perfluoroalkyl, aryl, substituted aryl, alkyl-aryl, or substituted alkyl-aryl; and
- $R_9$ is hydrogen, $C_1$–$C_6$ alkyl, $C_3$–$C_6$ branched alkyl, $C_1$–$C_6$ hydroxyalkyl, 4-hydroxybenzyl, 3-indolylymethylene, 4-imidazolylmethylene, $HSCH_2$—, $CH_3SCH_2CH_2$—, $H_2NC(=O)CH_2$—, $H_2NC(=O)CH_2CH_2$—, $HO_2CCH_2$—, $HO_2CCH_2CH_2$—, $H_2NCH_2CH_2CH_2CH_2$—, $H_2NC(=NH)NHCH_2CH_2CH_2$—, or taken together with $R_8$, —$CH_2CH_2CH_2$—;

or a pharmaceutically acceptable salt or ester form thereof.

8. A pharmaceutical composition comprising pharmaceutically effective amount of a compound of claim 1, or a pharmaceutically acceptable salt or ester form thereof, and a pharmaceutically acceptable excipient or carrier.

9. The method of claim 7 for the treatment of thrombosis or fibrinolytic impairment wherein the thrombosis or fibrinolytic impairment is associated with deep vein thrombosis in the mammal.

* * * * *